US010725028B2

(12) United States Patent
Inabe et al.

(10) Patent No.: US 10,725,028 B2
(45) Date of Patent: Jul. 28, 2020

(54) AUTOMATIC ANALYSIS DEVICE, AUTOMATIC ANALYSIS SYSTEM, AND AUTOMATIC ANALYSIS METHOD

(71) Applicant: HITACHI HIGH-TECHNOLOGIES CORPORATION, Tokyo (JP)

(72) Inventors: Toshiyuki Inabe, Tokyo (JP); Akihisa Makino, Tokyo (JP); Sakuichiro Adachi, Tokyo (JP); Chie Yabutani, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 0 days.

(21) Appl. No.: 15/749,197

(22) PCT Filed: Jun. 28, 2016

(86) PCT No.: PCT/JP2016/069171
§ 371 (c)(1),
(2) Date: Jan. 31, 2018

(87) PCT Pub. No.: WO2017/033562
PCT Pub. Date: Mar. 2, 2017

(65) Prior Publication Data
US 2018/0231537 A1 Aug. 16, 2018

(30) Foreign Application Priority Data
Aug. 26, 2015 (JP) ................. 2015-166877

(51) Int. Cl.
| G01N 33/48 | (2006.01) |
| G01N 33/542 | (2006.01) |
| G01N 21/82 | (2006.01) |
| G01N 21/51 | (2006.01) |
| G01N 21/25 | (2006.01) |
| G01N 21/27 | (2006.01) |
| G01N 33/52 | (2006.01) |
| G01N 33/86 | (2006.01) |
| G01N 35/00 | (2006.01) |
| G06G 7/58 | (2006.01) |

(52) U.S. Cl.
CPC ......... *G01N 33/542* (2013.01); *G01N 21/253* (2013.01); *G01N 21/272* (2013.01); *G01N 21/51* (2013.01); *G01N 21/82* (2013.01); *G01N 33/52* (2013.01); *G01N 33/86* (2013.01); *G01N 35/00663* (2013.01); *G01N 2035/00673* (2013.01); *G01N 2201/121* (2013.01); *G01N 2201/122* (2013.01); *G01N 2201/127* (2013.01); *G01N 2201/1242* (2013.01); *G01N 2201/1247* (2013.01)

(58) Field of Classification Search
None
See application file for complete search history.

(56) References Cited

U.S. PATENT DOCUMENTS

| 2007/0002309 A1 | 1/2007 | Yamamoto |
| 2007/0222973 A1 | 9/2007 | Hoshiko et al. |
| 2008/0070318 A1 | 3/2008 | Yamamoto et al. |
| 2010/0201987 A1 | 8/2010 | Iwawaki |
| 2012/0140230 A1 | 6/2012 | Miller |
| 2015/0044780 A1 | 2/2015 | Kurz et al. |
| 2016/0291048 A1 | 10/2016 | Makino et al. |

FOREIGN PATENT DOCUMENTS

| JP | 2007-010560 A | 1/2007 |
| JP | 2007-010562 A | 1/2007 |
| JP | 2007-263907 A | 10/2007 |
| JP | 2010-178983 A | 8/2010 |
| JP | 2013-501937 A | 1/2013 |
| JP | 2015-515005 A | 5/2015 |
| JP | 2015-135310 A | 7/2015 |
| WO | 2006/104005 A1 | 10/2006 |
| WO | 2015/093166 A1 | 6/2015 |

OTHER PUBLICATIONS

International Search Report of PCT/JP2016/069171 dated Sep. 27, 2016.
International Preliminary Report on Patentability and English translation of Written Opinion received in corresponding International Application No. PCT/JP2016/069171 dated Mar. 8, 2018.
Extended European Search Report received in corresponding European Application No. 16838909.6 dated Jan. 28, 2019.

*Primary Examiner* — Eric S Dejong
(74) *Attorney, Agent, or Firm* — Mattingly & Malur, PC

(57) ABSTRACT

The automatic analysis device is provided with (1) a measurement mechanism having a light measuring unit having a reaction container in which the sample is dispensed, a light source which emits light to the reaction container, and a detection unit that detects scattered light from the sample in the reaction container, (2) an amplifier circuit unit having an adder-subtractor that adds or subtracts a correction signal to or from a first measurement signal from the detection unit, and an amplifier circuit which amplifies the output signal by the adder-subtractor at a fixed amplification rate to output a second measurement signal, and (3) an arithmetic operation unit which calculates the correction signal on the basis of a difference between the signal level of the second measurement signal and a target value, and which executes an analysis action based on the second measurement signal after correction by means of the correction signal.

16 Claims, 10 Drawing Sheets

[Fig. 1]
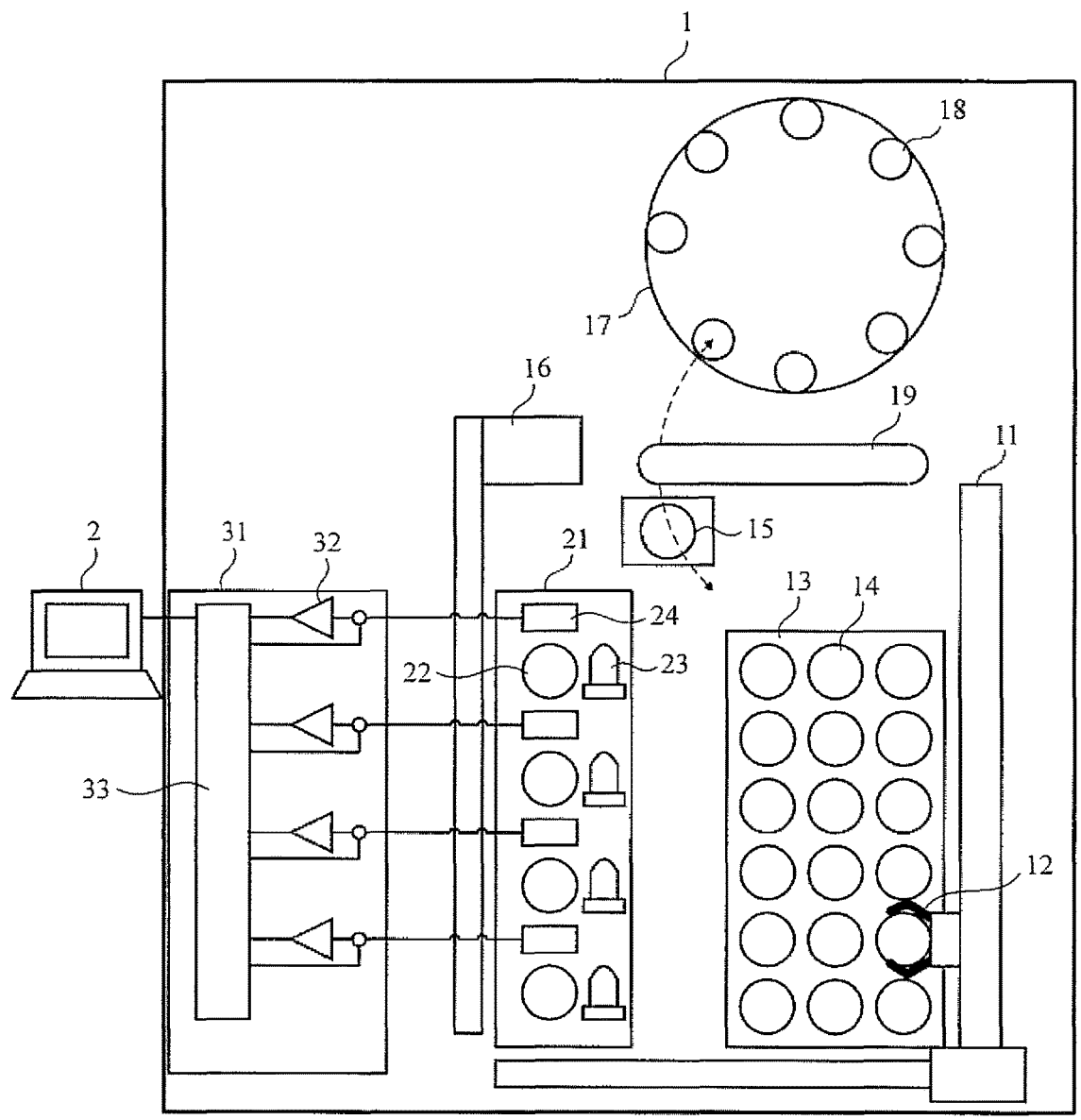

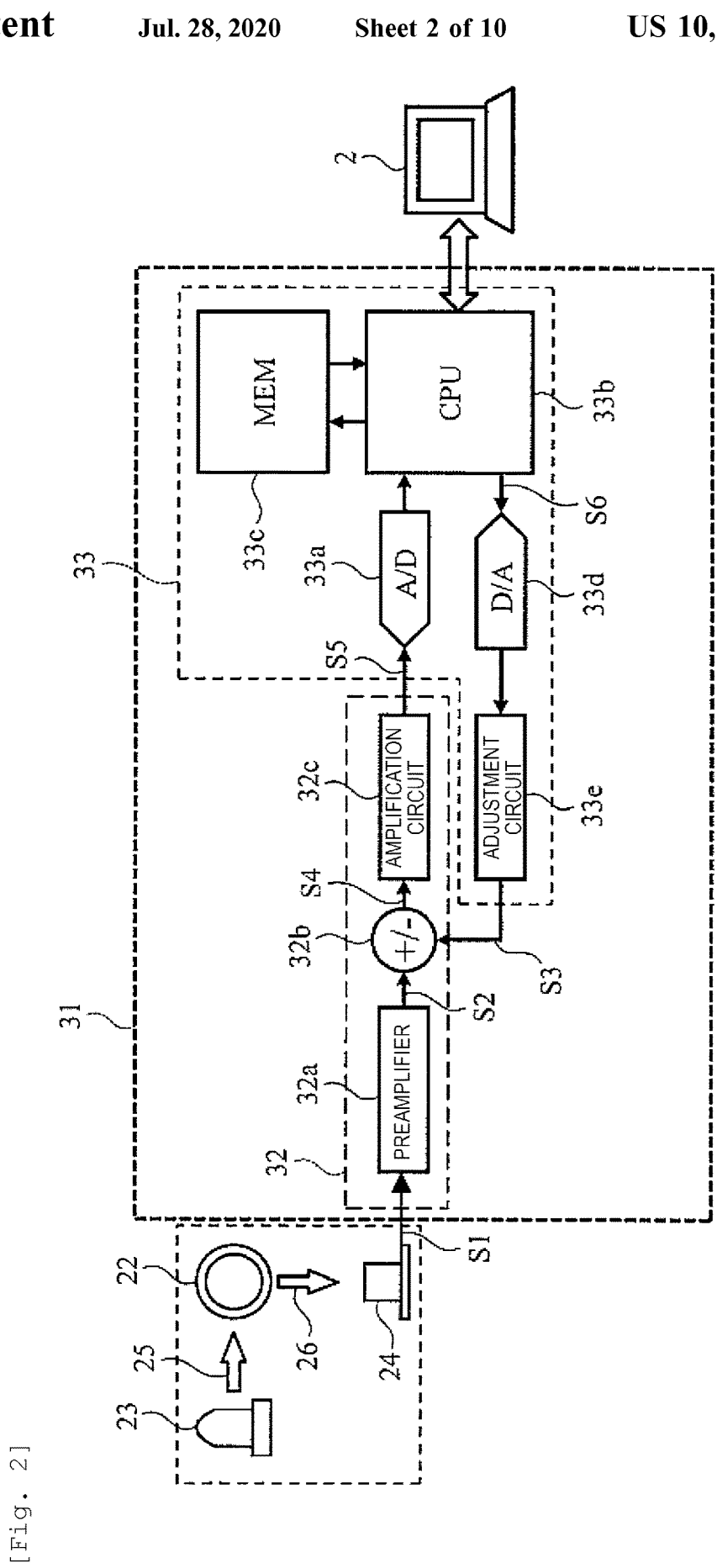
[Fig. 2]

[Fig. 3]
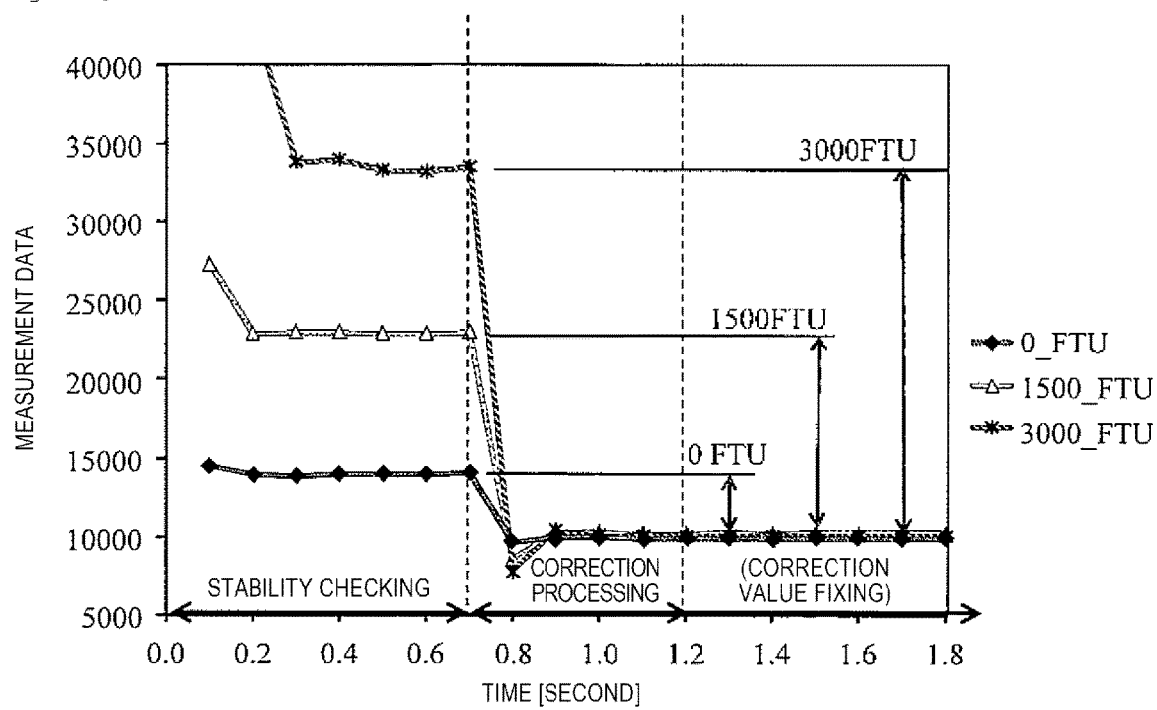

[Fig. 4]
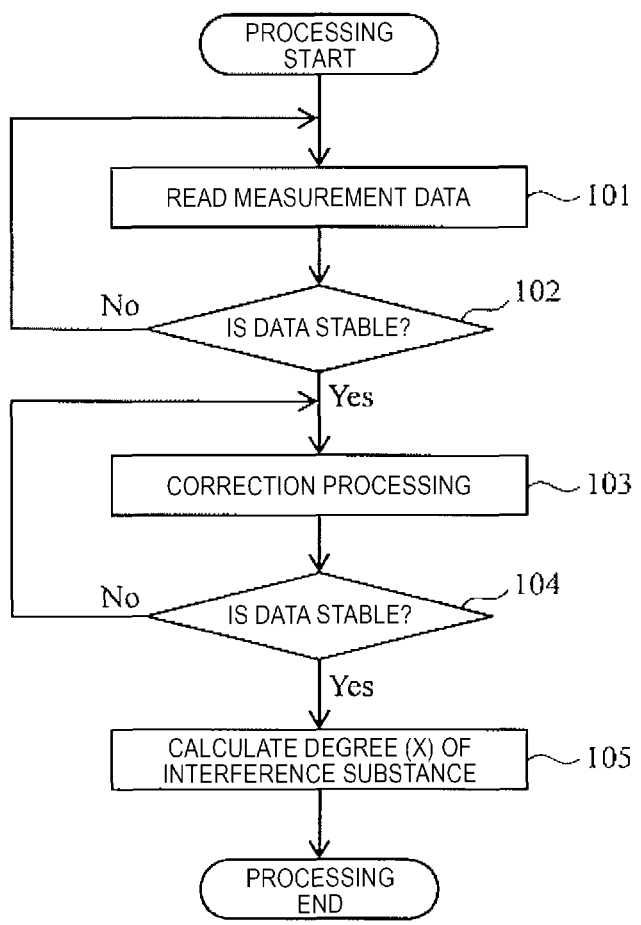
[Fig. 5]
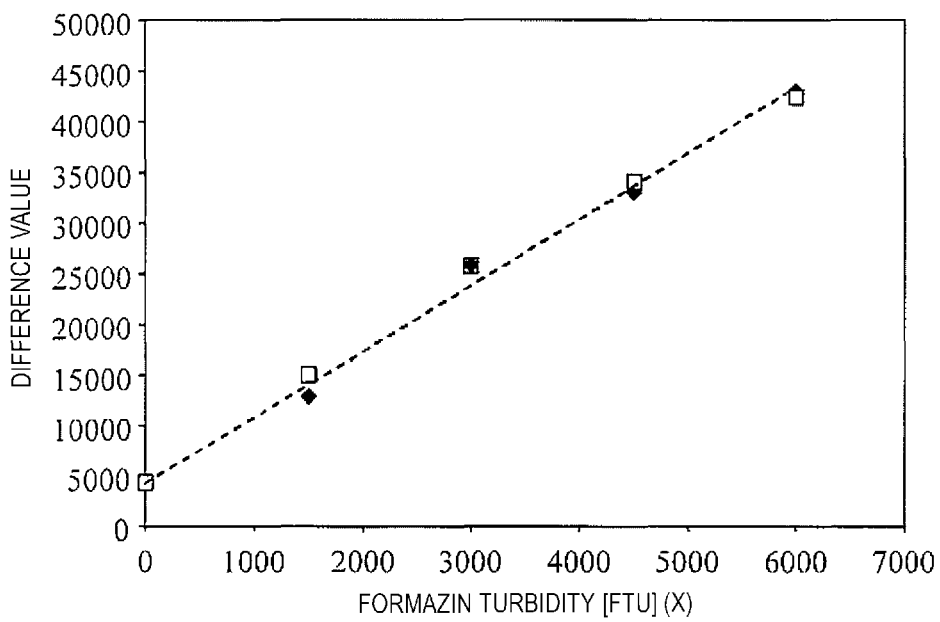

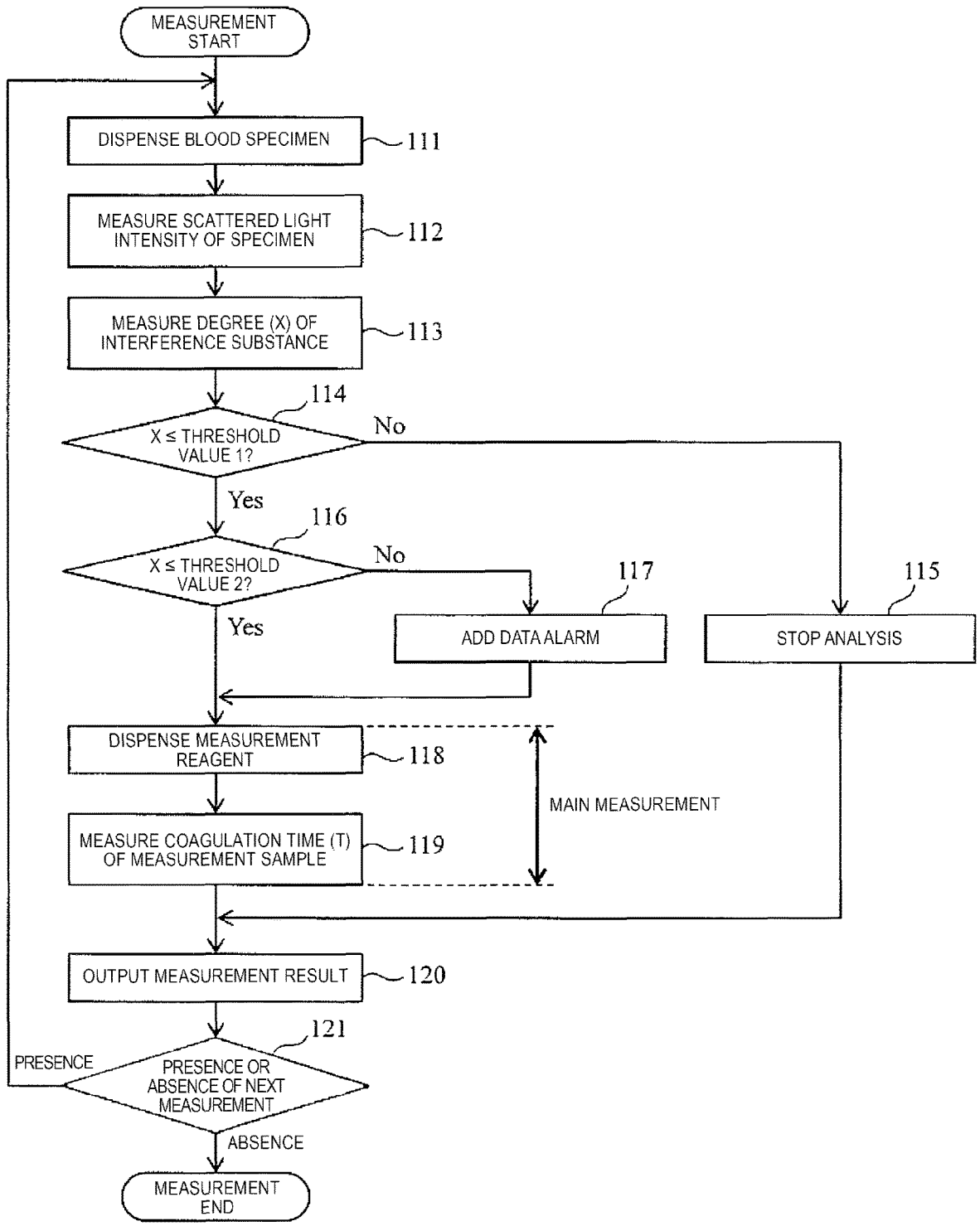
[Fig. 6]

[Fig. 7]
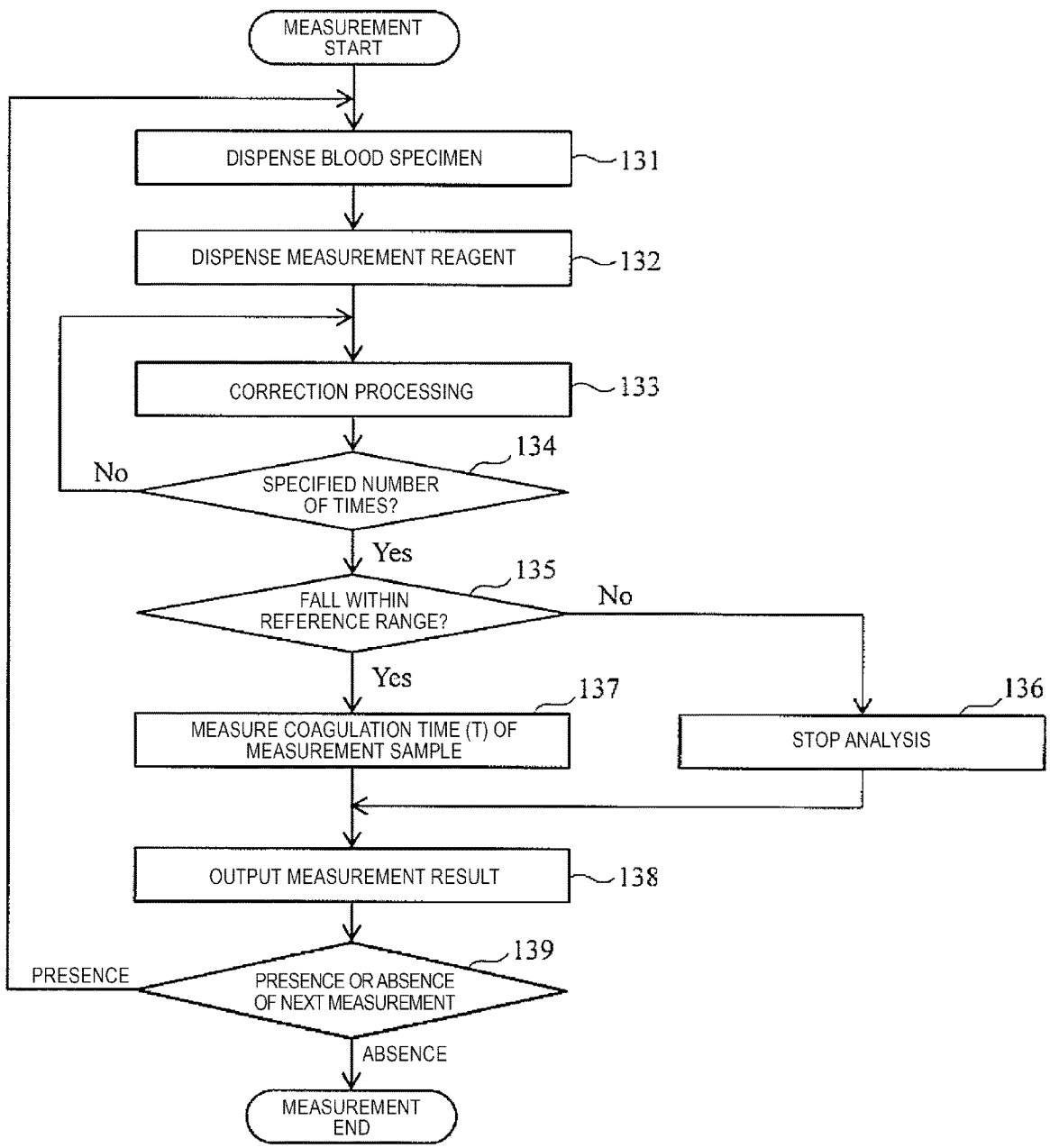

[Fig. 8]
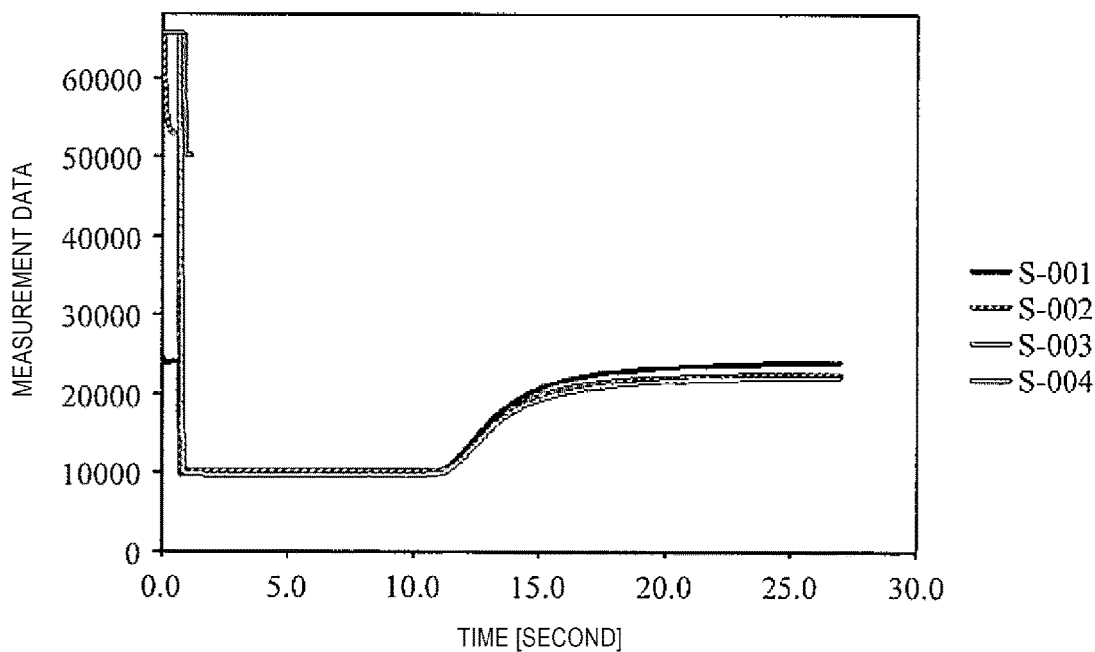
[Fig. 9]
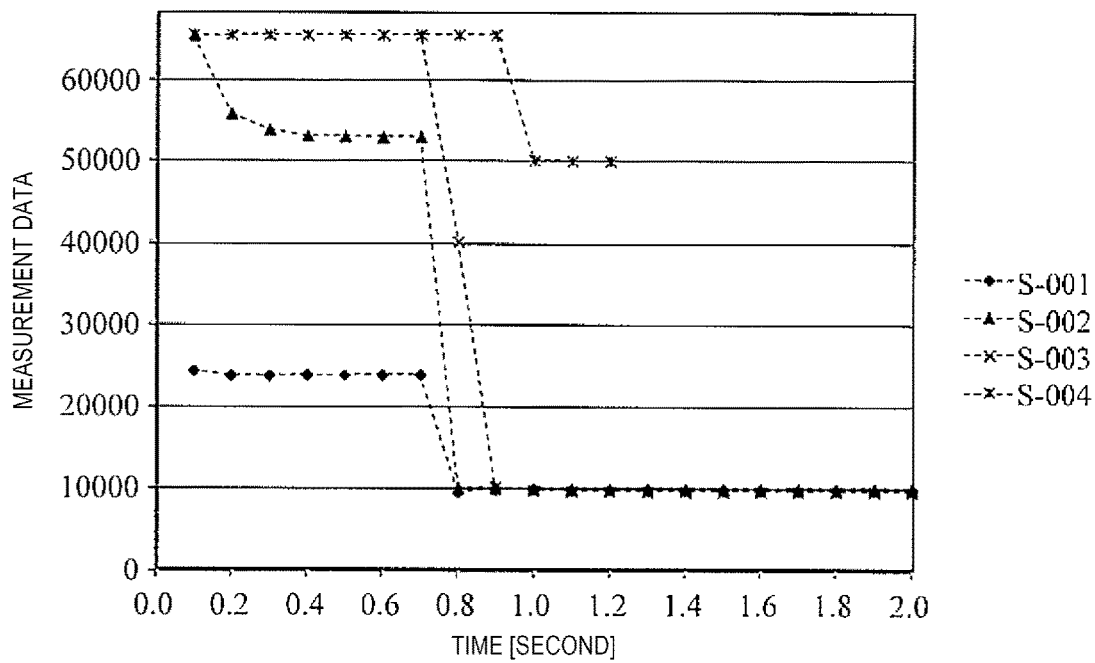

[Fig. 10]
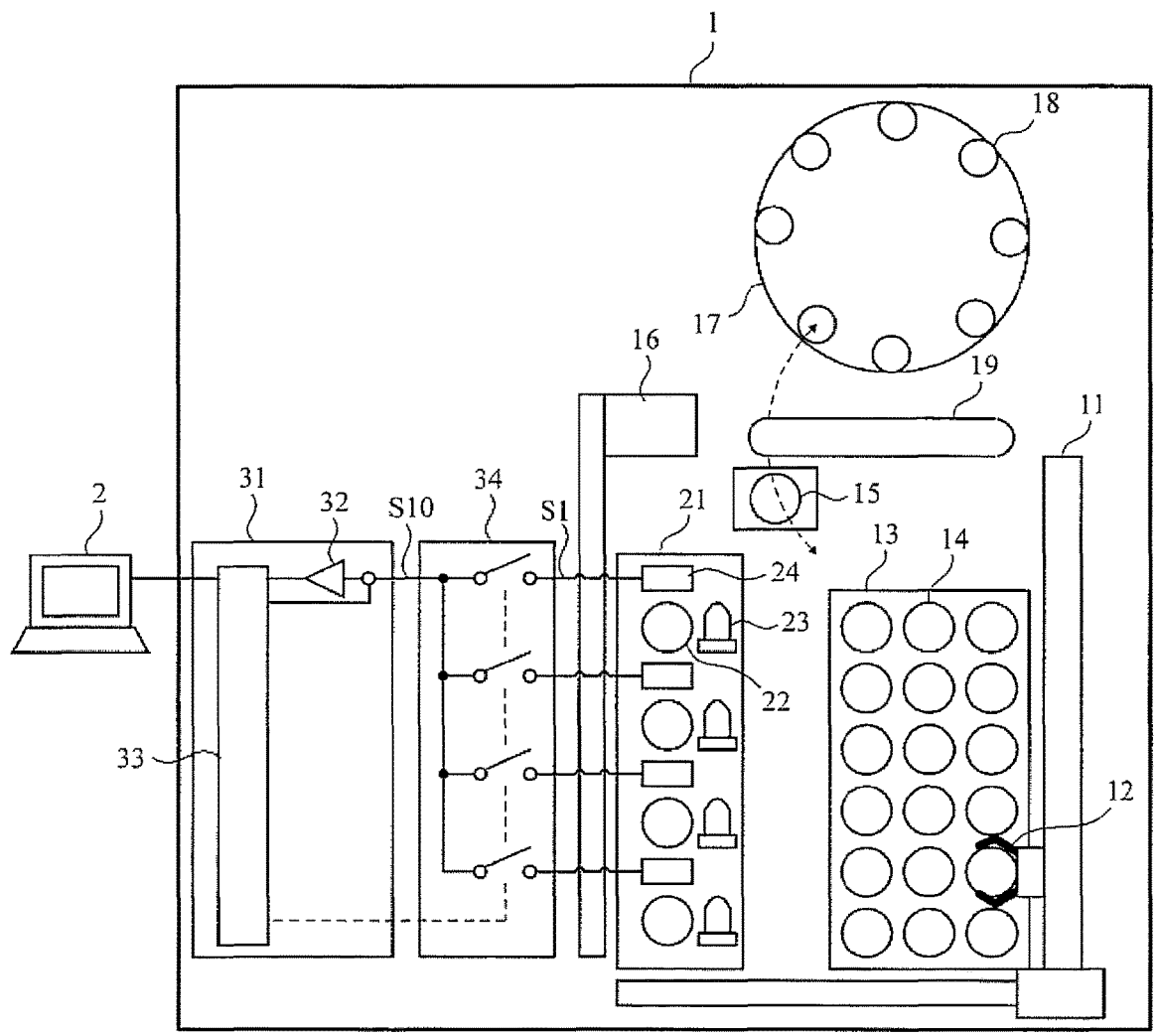

[Fig. 11]
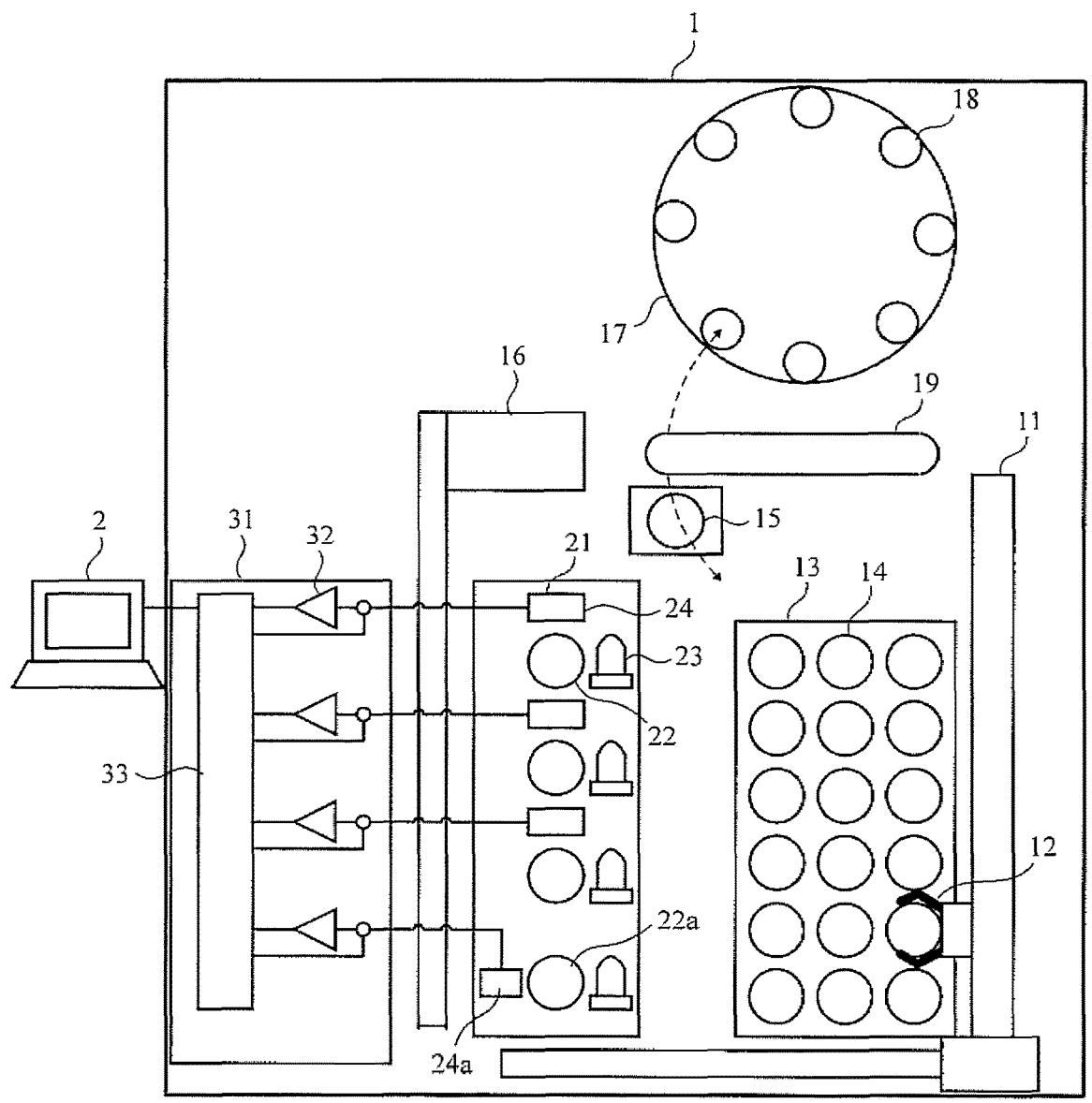

[Fig. 12]
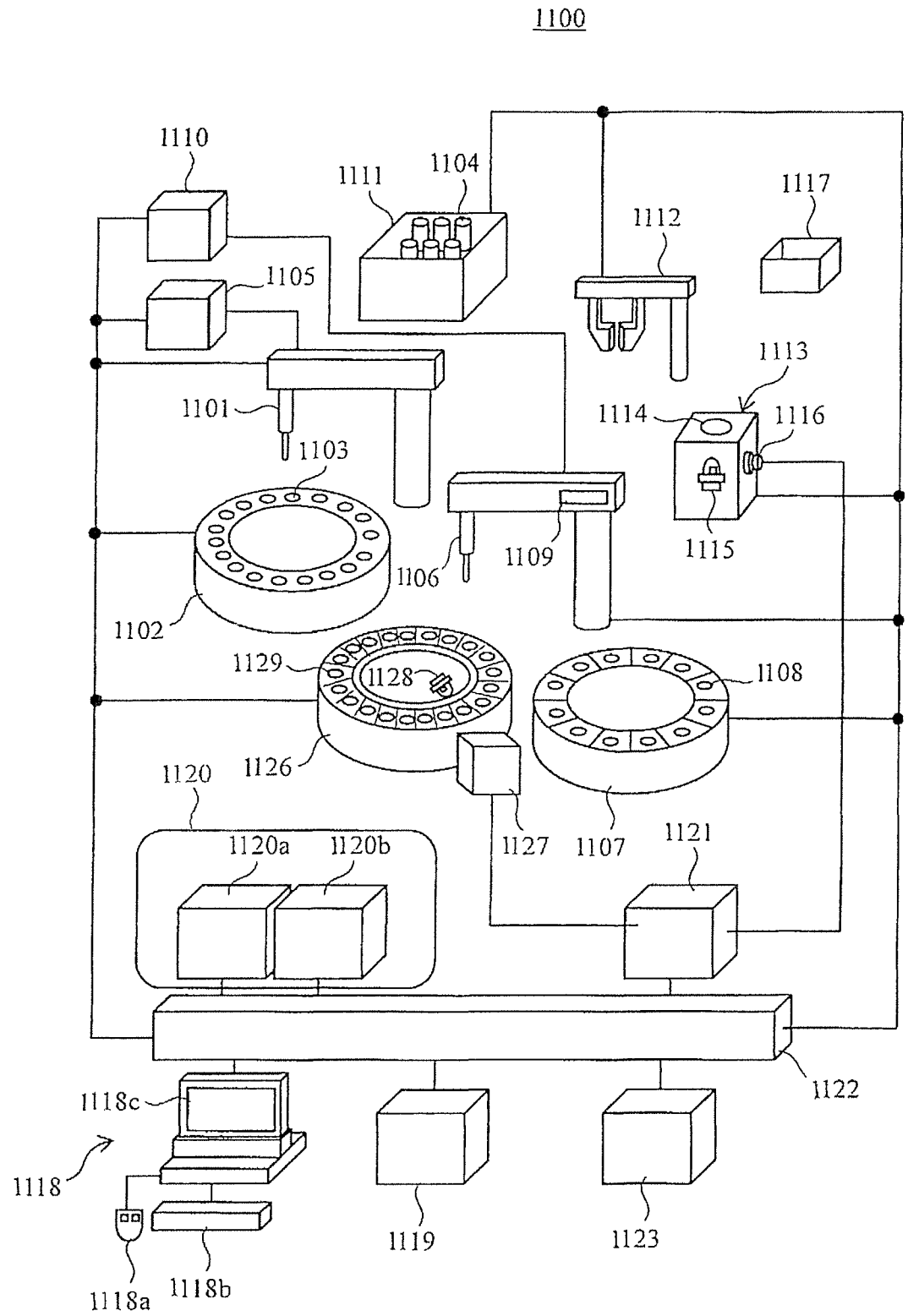

AUTOMATIC ANALYSIS DEVICE, AUTOMATIC ANALYSIS SYSTEM, AND AUTOMATIC ANALYSIS METHOD

TECHNICAL FIELD

The present invention relates to an automatic analysis device, an automatic analysis system, and an automatic analysis method.

BACKGROUND ART

A blood coagulation analysis device is known which analyzes blood coagulation time by adding a reagent for coagulating blood to a blood specimen, preparing a coagulation analysis sample, and optically measuring a coagulation reaction process of the coagulation analysis sample. In the blood coagulation analysis, there is a case where the blood coagulation analysis is not accurately performed by an optical measurement being affected by interference substances (substances coexisting in the sample together with the target substance to be tested and optically interfering with the measurement of the target substance) such as hemoglobin, bilirubin, and chyle contained in the coagulation analysis sample. If light having a long wavelength is used for measurement, although it is not affected by hemoglobin and bilirubin, the influence of chyle also decreases, on the other hand, the measurement sensitivity decreases. Therefore, in the blood coagulation analysis device of the related art, light having a wavelength around 660 [nm], which is less susceptible to the influence of interference substances moderately and has suitable measurement sensitivity, is used for measurement. However, even when light having a wavelength around 660 [nm] is used for measurement, the influence of chyle cannot be ignored. Therefore, efforts have been made to quantify the degree to which these interference substances are contained in the specimen and to eliminate the influence thereof.

For example, PTL 1 discloses a technique which measures the content degree of interference substances using optical information (lag phase) from mixing of a coagulation analysis reagent into the blood specimen until before the coagulation reaction is shown by light from a coagulation analysis sample obtained by mixing a coagulation analysis reagent into a blood specimen is received by a first light receiving portion to acquire temporal optical information. According to this method, since the degree of the interference substance in the blood specimen can be measured and the blood specimen is diluted with the coagulation analysis reagent, a measurement range of the degree of the interference substance can be expanded.

In addition, PTL 1 described above also discloses a technique for acquiring optical information by receiving light from the blood specimen before a coagulation analysis reagent is mixed into the blood specimen. According to this method, since the content degree of interference substances in the blood specimen can be measured before the coagulation analysis reagent is mixed with the blood specimen, in a case where the content degree of interference substances in the blood specimen is large, the mixing of the coagulation analysis reagent into the blood specimen can be stopped. Therefore, wasteful consumption of the coagulation analysis reagents can be suppressed.

PTL 2 discloses a technique which adjusts an amplification rate of a detection circuit by a light source having a plurality of wavelengths and electronic volumes corresponding thereto in order to detect the presence or absence, type, the content degree, or the like of interference substances in a specimen before mixing a coagulation analysis reagent into the blood specimen.

CITATION LIST

Patent Literature

PTL 1: JP-A-2007-263907
PTL 2: Pamphlet of International Publication No. 2006/104005

SUMMARY OF INVENTION

Technical Problem

However, in the former method described in PTL 1, since the degree of interference substance is measured using the optical information before the coagulation analysis sample after mixing the coagulation analysis reagent into the blood specimen shows a coagulation reaction, in a case where the measurement has to be stopped due to the influence of the interference substances contained in the blood specimen, the coagulation analysis reagent is wasted.

In addition, in the latter method described in PTL 1, since the degree of interference substances is measured using optical information that is acquired by receiving light from a blood specimen before mixing a coagulation analysis reagent into the blood specimen (since blood specimen is not diluted with coagulation analysis reagent as in the former method), when the degree of the interference substances in the blood specimen is large, the degree of the interference substances is outside the measurement range and thus there is a case where the degree of the interference substance cannot be measured.

On the other hand, in a case of PTL 2, even if the degree of the interference substance in the blood specimen is large, the degree of the interference substance can be measured by adjusting the amplification rate of the detection circuit with the electronic volume. However, if a coagulation time of the blood specimen is measured with the same amplification rate as when measuring the degree of the interference substance, the sensitivity at the time of measurement differs according to the degree of the interference substance and thus an error is generated in the measurement result. In order to solve this problem, it is necessary to switch the wavelength of the light source at the time of coagulation time measurement (main measurement), or to provide a light measuring unit used for measuring the degree of interference substance separately from a light measuring unit used for main measurement and thus the configuration and control contents of the device become complicated.

Therefore, the inventor of the present invention provides a mechanism that can expand the measurement range of the degree of interference substances regardless of before or after mixing of the reagent into the specimen and further the measurement of the degree of the interference substance and the measurement of the specimen can be realized under the same measurement condition.

Solution to Problem

In order to solve the problem described above, the present invention adopts configurations described in the claims, for example. Although the present specification includes a plurality of means for solving the problems described above, as an example thereof, there is provided "an automatic analysis device including: (1) a measurement mechanism that has a light measuring unit in which a reaction container into which a specimen is dispensed is erected, a light source which irradiates the reaction container with light, and a detection unit which detects scattered light from the specimen in the reaction container; (2) an amplification circuit unit that has an adder/subtracter which adds or subtracts a correction signal to/from a first measurement signal from the detection unit and an amplification circuit which amplifies an output signal from the adder/subtracter with a fixed amplification rate and outputs the amplified output signal as a second measurement signal; (3) an arithmetic operation unit that calculates the correction signal based on a difference between a signal level of the second measurement signal and a target value thereof and executes an analysis operation based on the second measurement signal after the correction by the correction signal; and (4) a control unit that controls operations of the measurement mechanism, the amplification circuit unit and the arithmetic operation unit".

Advantageous Effects of Invention

According to the present invention, the measurement range of the interference substance can be expanded regardless of before or after mixing of the reagent into the specimen and further the degree of the interference substance and the measurement of the specimen can be measured under the same measurement condition. The problems, configurations, and effects other than those described above will be clarified by the following description of the embodiments.

BRIEF DESCRIPTION OF DRAWINGS

FIG. 1 is a diagram illustrating a schematic configuration of a blood coagulation analysis device according to Example 1.
FIG. 2 is a view for explaining the internal configuration of a signal processing portion constituting the blood coagulation analysis device.
FIG. 3 is a view illustrating a measurement result example in Example 1.
FIG. 4 is a flowchart for explaining a processing operation of an arithmetic operation unit constituting a signal processing portion.
FIG. 5 is a view for explaining a relationship between the degree (X) of interference substances and the difference value (correction amount).
FIG. 6 is a flowchart for explaining a measurement procedure by the blood coagulation analysis device according to Example 1.
FIG. 7 is a flowchart for explaining a measurement procedure by a blood coagulation analysis device according to Example 2.
FIG. 8 is a view illustrating an example of measurement results in Example 2.
FIG. 9 is an enlarged view illustrating a portion of the measurement result example illustrated in FIG. 8.
FIG. 10 is a view illustrating a schematic configuration of a blood coagulation analysis device according to Example 3.
FIG. 11 is a diagram illustrating a schematic configuration of a blood coagulation analysis device according to Example 4.
FIG. 12 is a diagram illustrating a schematic configuration of a composite type automatic analysis device according to Example 5.

DESCRIPTION OF EMBODIMENTS

Hereinafter, embodiments of the present invention will be described with reference to the drawings. The embodiments of the present invention are not limited to the examples described below and various modifications are possible within the scope of the technical idea thereof.

(1) Example 1

(1-1) Overall Configuration
In this embodiment, a blood coagulation analysis device which is an example of an automatic analysis device will be described. FIG. 1 illustrates a schematic configuration of a blood coagulation analysis device 1 according to this example. The blood coagulation analysis device 1 is externally connected to a control device 2 configured as a calculator. The blood coagulation analysis device 1 and a control device 2 constitute an automatic analysis system.

The operation of each portion constituting the blood coagulation analysis device 1 is controlled by the control device 2. The control device 2 is used for controlling the operation of each portion constituting the blood coagulation analysis device 1 such as an operation of a reaction container transfer mechanism 11, an operation of a reaction container holding mechanism 12, an operation of a specimen dispensing portion 15, an operation of a coagulation analysis reagent dispensing mechanism 16, an operation of a specimen erection portion 17, an operation of a specimen dispensing mechanism 19, an operation of a measurement mechanism 21, an operation of a signal processing portion 31, an operation of a pump (not illustrated), an operation of a washing mechanism (not illustrated), and an washing water supply operation, the condition setting thereof, or the like. The control device 2 may be mounted inside a casing of the blood coagulation analysis device 1.

The reaction container holding mechanism 12 attached to the reaction container transfer mechanism 11 selectively grabs one reaction container or one of a plurality of reaction containers 14 erected on the reaction container erection portion 13 and transfer the grabbed reaction container to the specimen dispensing portion 15 or to the light measuring unit 22. The specimen dispensing mechanism 19 sorts out the blood specimen to be measured from one or a plurality of specimen containers 18 erected on the specimen erection portion 17 and dispenses the sorted blood specimen into the reaction container erected on the specimen dispensing portion 15. The coagulation analysis reagent dispensing mechanism 16 dispenses the coagulation analysis reagent according to the measurement item to the reaction container 14.

The measurement mechanism 21 is provided with one or more (four in FIG. 1) light measuring units 22. One or more (one in FIG. 1) light sources 23 for emitting irradiation light and one or more (one in FIG. 1) light receiving portions 24 for receiving scattered light from the light measuring units 22 are disposed on the light measuring unit 22. The measurement signal from the light receiving portion 24 is processed in the amplification circuit unit 32 and the arithmetic operation unit 33 of the signal processing portion 31 and the processing result thereof is displayed on a user interface screen of a display device provided in the control device 2.

(1-2) Internal Configuration of Signal Processing Portion 31
FIG. 2 illustrates the internal configuration of the signal processing portion 31. As described above, the signal processing portion 31 includes the amplification circuit unit 32 and the arithmetic operation unit 33.

The amplification circuit unit 32 includes a preamplifier 32a, an adder/subtracter 32b, and an amplification circuit 32c. On the other hand, the arithmetic operation unit 33 includes an analog/digital conversion circuit 33a, a CPU 33b, a memory 33c, a digital/analog conversion circuit 33d, and an adjustment circuit 33e.

The measurement signal S1 outputted from the light receiving portion 24 is primarily amplified by the preamplifier 32a and then input to the adder/subtracter 32b. The adder/subtracter 32b adds/subtracts the correction signal S3 fed back from the arithmetic operation unit 33 with respect to the measurement signal S2 input from the preamplifier 32a of the preceding stage and outputs the correction signal to the amplification circuit 32c of the subsequent stage. Here, the amplification circuit 32c secondarily amplifies a corrected measurement signal S4 output from the adder/subtracter 32b. Meanwhile, in the initial state (stability confirmation period described below), the amplification degree in the adjustment circuit 33e is set to the initial value (zero). Therefore, a signal level of the corrected measurement signal S5 output from the amplification circuit 32c in the initial state is equal to the signal level obtained by amplifying the measurement signal S1 of the light receiving portion 24 by an integrated value of the amplification degree (fixed value) of the preamplifier 32a and the amplification degree (fixed value) of the amplification circuit 32c.

A corrected measurement signal S5 output from the amplification circuit 32c is converted into a digital value by the analog/digital conversion circuit 33a and then processed by the CPU 33b. In addition, the digital value obtained by converting the corrected measurement signal S5 is stored in the memory 33c over time. The CPU 33b uses the digital value stored in the memory 33c and executes the measurement processing of the scattered light intensity of the specimen and the measurement processing of the degree (X) of the interference substance. Specific processing contents will be described below.

A correction data S6 which gives the magnitude of the degree (X) of the interference substance calculated by the CPU 33b is converted into an analog signal by the digital/analog conversion circuit 33d and then output to the adjustment circuit 33e. The adjustment circuit 33e converts the signal level of the input analog signal in order to be equivalent to the input level of the amplification circuit 32c and outputs the converted input analog signal as the correction signal S3.

The adjustment circuit 33e has an initial value and a predetermined value as an adjustment value. The adjustment value is switched from the initial value to a predetermined value according to an instruction from the CPU 33b. The adjustment circuit 33e outputs the level-adjusted correction signal S3 to the adder/subtracter 32b. By the addition and subtraction performed by the adder/subtracter 32b, the influence of the degree (X) of the interference substance contained in the measurement signal S1 output from the light receiving portion 24 is removed.

(1-3) Internal Processing of Signal Processing Portion 31

In the initial state immediately after the start of the measurement, the digital value (measurement data) of the corrected measurement signal S5 representing the scattered light intensity measured by the light receiving portion 24 is sequentially stored in the memory 33c. The corrected measurement signal S5 at this stage includes not only the intensity component of the scattered light from the specimen but also the intensity component of the scattered light from the unknown interference substance. "A stability confirmation period" in FIG. 3 corresponds to time transition of the measurement data immediately after the start of measurement. FIG. 3 illustrates a case where the degree (X) of interference substances is 0 (zero) [FTU], 1500 [FTU], and 3000 [FTU]. It can be seen that as the degree (X) of the interference substance increases, the value of the measurement data increases.

However, for a while from the start of the measurement, the fluctuating portion appears in the measurement data. Therefore, it is necessary to calculate the degree (X) of the interference substance after the timing at which the transition of the measurement data becomes stable. Therefore, as illustrated in FIG. 4, the CPU 33b sequentially reads measurement data from the memory 33c (process 101) and determines whether or not the data is stable (process 102). For example, measurement data is read for each 0.1 seconds. Whether or not the data is stable can be determined, for example, based on whether or not the deviation of two or more consecutive or intermittent data stored in the memory 33c is within a predetermined range. In the example of FIG. 3, it is determined that the measurement data is stable at the time of 0.7 seconds from the start of measurement.

In a case where that the time length (for example, 0.7 seconds in the case of FIG. 3) required for the measurement data to be stable is known by prior measurement, the CPU 33b monitors only the elapsed time from the start of the measurement, it can be determined whether or not the measurement data is stable. In this case, it is unnecessary to read the measurement data of the process 101.

When the transition of the measurement data is stable, the CPU 33b executes the correction processing (processing 103). In this process, the CPU 33b calculates the difference value between the target value of the preset measurement value ("1000" in the case of FIG. 3) and the latest measurement data, converts the calculated difference value to a tentative value (corrected measurement signal S5) corresponding to the degree (X) of interference substance, and outputs it to the digital/analog conversion circuit 33d. Here, for the conversion from the difference value to the degree (X) of the interference substance, a relational expression established between the difference value obtained in advance and the degree (X) of the interference substance is used. This relational expression is generally expressed as a linear equation.

FIG. 5 illustrates an example of a relationship between the difference value and the degree (X) of the interference substance. In a case of FIG. 5, the vertical axis represents difference values, and the horizontal axis represents formazin turbidity (degree (X) of chyle which is an interference substance). In the drawing, the broken line approximating the sample point corresponds to the relational expression described above. The relationship illustrated in FIG. 5 is obtained by measuring the degree (X) of the known interference substance and the difference value in advance. A conversion table that satisfies this relational expression is stored in the CPU 33b. Although the relationship between the degree (X) of interference substances and the difference value is desirably determined every time prior to the measurement, the relationship thereof may be obtained for each measurement interval (for example, once every several times) according to the usage situation.

Returning to the description of FIG. 4, During the execution of the correction process, the CPU 33b determines whether or not the digital value of the corrected measurement signal S5 whose signal level is reduced by the correction signal S3 is stable (process 104). For this determination process, a method similar to the method described above is used. This determination process is continued until the corrected measurement signal S5 obtained by subtracting the correction signal S3 from the measurement signal S2 is stable to a value close to the target value. A time of 0.7 seconds to 1.2 seconds from the start of measurement corresponds to the example of FIG. 3.

The CPU 33b determines the degree (X) of the interference substance at the end of the correction processing period as a correction value (fixed) to be used in the main measurement and outputs the degree thereof as the correction data S6 during the main measurement (processing 105). Upon shifting to this measurement (in the case of FIG. 3, 1.2 seconds or later), the CPU 33b executes the control operation of each portion and outputs the measurement result such as the coagulation time of the measurement sample. In this measurement (correction value fixed period of FIG. 3), the confirmed correction value is used as it is.

(1-4) Measurement Operation by Blood Coagulation Analysis Device 1

FIG. 6 illustrates a measurement procedure by the blood coagulation analysis device 1. Prior to the start of the measurement, various conditions relating to the measurement are set in advance by the control device 2 in the blood coagulation analysis device 1.

The blood coagulation analysis device 1 starts a measurement operation based on an instruction from the control device 2. First, the control device 2 executes a blood specimen dispensing process (process 111). Here, the control device 2 transfers the reaction container 14 erected on the reaction container erection portion 13 to the specimen dispensing portion 15 using the reaction container holding mechanism 12 mounted on the reaction container transfer mechanism 11. Thereafter, under the control of the control device 2, the blood coagulation analysis device 1 fractionates the blood specimen to be measured from the specimen container 18 using the specimen dispensing mechanism 19 and dispenses the blood specimen to a reaction container 14 erected on the specimen dispensing portion 15.

Next, the control device 2 executes the measurement process (process 112) of the scattered light intensity of the specimen. Here, the control device 2 transfers the reaction container 14 into which the blood specimen is dispensed from the specimen dispensing portion 15 to the light measuring unit 22 using the reaction container holding mechanism 12 mounted on the reaction container transfer mechanism 11. Thereafter, the blood coagulation analysis device 1 causes the light source 23 to generate irradiation light 25 and irradiates the reaction container 14 with the irradiation light. At the same time, the blood coagulation analysis device 1 receives the scattered light 26 scattered by the blood specimen in the reaction container 14 by the light receiving portion 24 disposed in the vicinity of the reaction container 14. The light receiving portion 24 outputs a measurement signal S1 corresponding to the magnitude of the received scattered light 26.

As the wavelength of a measurement light, a long wavelength which is unlikely to be affected by interference substances (hemoglobin, bilirubin) contained in the blood specimen is used. In this example, a light source 23 that emits irradiation light 25 having a wavelength of 660 [nm] to 700 [nm], which has relatively high measurement sensitivity in this measurement, is used. As the light receiving portion 24, it is preferable to use a light receiving element having high light receiving sensitivity with respect to the wavelength to be used. At the time of the measurement process 102, as described above, the influence of the degree (X) of the unknown interference substance is included in the measurement signal S1.

Next, the control device 2 executes the measurement process (process 113) of the degree (X) of the interference substance. Here, the signal processing portion 31 calculates the difference value between the digital value of the corrected measurement signal S5 and the target value, and removes the influence of the degree (X) of the interference substance which is conceived to the difference value from the measurement signal S2. When the digital value of the corrected measurement signal S5 is stable, the degree (X) of the interference substances contained in the blood specimen is measured.

Subsequently, the control device 2 compares the measured degree (X) of the interference substance with the threshold 1 (process 114). The threshold value 1 is a value of the degree (X) of the interference substance which affects the present measurement and is set in advance. As the threshold value 1, the manufacturer may prepare an initial setting value, or the user may input the initial setting value through the user interface screen of the display device provided in the control device 2. In a case where the degree (X) of the interference substance is larger than the threshold 1 (in a case where degree (X) of interference substance is high and influence on this measurement is assumed), the control device 2 stops the analysis (main measurement) (processing 115). In this case, since the analysis (main measurement) is stopped before dispensing the measurement reagent to the blood specimen, the waste of the measurement reagent can be suppressed. In addition, at this time, an alarm indicating that the analysis (main measurement) is stopped or an alarm indicating that the degree (X) of the interference substance is high may be outputted.

On the other hand, in a case where the degree (X) of the interference substance is equal to or less than the threshold value 1, the control device 2 compares the degree (X) of the interference substance with the threshold value 2 (process 116). The threshold value 2 is a value used for determining that the degree (X) of the interference substance does not affect the main measurement, but is higher to a certain extent, and is set in advance. As the threshold value 2, the manufacturer may prepare the initial setting value, or the user may input the initial setting value through the user interface screen of the display device provided in the control device 2.

Here, in a case where the degree (X) of the interference substance is larger than the threshold 2, the control device 2 adds a data alarm (process 117). At this time, the control device 2 notifies the user through the user interface screen of the display device or the speaker that the degree (X) of the interference substance is high to a certain extent. The control device 2 may display the degree (X) of interference substances, as necessary.

In a case where the degree (X) of the interference substance is equal to or less than the threshold value 2 or after the data alarm addition process 117 is executed, the control device 2 dispenses the measurement reagent, to the blood specimen determined to be capable of performing this measurement (process 118). Next, the control device 2 measures a coagulation time (T) of the measurement reagent (process 119) using the measurement data. In other words, the control device 2 measures the time (coagulation time (T)) from the dispensing of the measurement reagent to the detection of the coagulation. Thereafter, the control device 2 displays the measured coagulation time (T) or the fact that the measurement is stopped on the user interface screen of the display device (measurement result output process 120).

Thereafter, the control device 2 determines the presence or absence of a blood specimen to be measured next (process 121). In a case where there is a blood specimen to be measured next, the next blood specimen is dispensed into the reaction container 14 (process 111), and in a case where is no blood specimen to be measured next, a series of measurement process is ended.

(1-5) Effect of Example

Since the blood coagulation analysis device 1 subtracts the correction signal S3 from the measurement signal S2 to obtain the corrected measurement signal S5, even before mixing the measurement reagent into the blood specimen, the measurement range of the degree (X) of interference substance Can be expanded. Therefore, even in a case where the degree (X) of the interference substance is high, it is possible to measure the coagulation time by performing this measurement.

In addition, in a case where the degree (X) of interference substance is high and the influence on this measurement is assumed, this measurement can be stopped before mixing the measurement reagent into the blood specimen. As a result, it is possible to suppress the waste of the measurement reagent. In addition, in the blood coagulation analysis device 1, even in a case where the degree (X) of the interference substance is high to a certain extent, the present measurement can be performed without changing the measurement time and the measurement condition of the degree (X) of the interference substance. In other words, as in a case of PTL 2, there is a need to switch the electronic volume, to switch the wavelength of the irradiation light 25, or to separately provide an optical system for measurement of the degree (X) of interference substance and an optical system for main measurement. Therefore, it is possible to improve the measurement efficiency.

(2) Example 2

In Example 1 described above, although a case where the measurement reagent is dispensed after the correction process is performed to measure the degree (X) of the interference substance the main measurement is described, in this example, a case where the correction process is performed after the measurement reagent is dispensed and then the main measurement is executed is described. The device configuration of the blood coagulation analysis device 1 is the same as that of the first embodiment.

FIG. 7 illustrates a measurement procedure of the blood coagulation analysis device 1 according to this example. The blood coagulation analysis device 1 starts a measurement operation based on an instruction from the control device 2. First, the control device 2 dispenses the blood specimen into the reaction container 14 (process 131). Specifically, the control device 2 uses the reaction container holding mechanism 12 to transfer the reaction container 14 erected in the reaction container erection portion 13 to the specimen dispensing portion 15, and then uses the specimen dispensing mechanism to fractionate the blood specimen from the specimen container 18, and then dispenses the fractionated blood specimen into the reaction container 14 erected in the specimen dispensing portion 15.

Next, the control device 2 dispenses the measurement reagent to the reaction container 14 (process 132). Specifically, the control device 2 transfers the reaction container 14 into which the blood specimen is dispensed from the specimen dispensing portion 15 to the light measuring unit 22 using the reaction container transfer mechanism 11, and then dispense the coagulation analysis reagent to the reaction container 14 using the coagulation analysis reagent dispensing mechanism 16 according to the measurement item. Thereafter, the control device 2 irradiates the irradiation light 25 from the light source 23 to the coagulation analysis sample in which the blood specimen and the coagulation analysis reagent are mixed to each other by the discharge pressure of the reagent at the time of dispensing in the same manner as in Example 1, and then scattered light 26 scattered by the blood specimen in the reaction container 14 is received by the light receiving portion 24.

There is a certain period of time (lag phase) from when the blood specimen and the coagulation reagents are mixed to each other until the coagulation reaction appears. In this example, the correction process (process 133) for approximating the digital value of the corrected measurement signal S5 to a preset target value is repeated by the specified number of times using this lag phase (process 134). Instead of executing the prescribed number of times of correction processes, as in the method described in Example 1, it is possible to use a method of checking whether or not the digital value of the corrected measurement signal S5 is stable in the vicinity of the target value or a method of checking the progress of the lag phase time can be used.

FIG. 8 illustrates an example of measurement data after the correction process is performed a specified number of times during the lag phase. S-001, S-002, S-003 and S-004 in the drawing indicate different blood specimens. FIG. 9 is an enlarged view of measurement results of 0.1 second to 2.0 seconds in the transition of the measurement data illustrated in FIG. 8. In FIG. 8 and FIG. 9, the target value is set as 10000 counts and it is indicated a case where the correction process is repeatedly performed between 0.7 seconds and 1.0 seconds.

The control device 2 captures the measurement data after the correction process from the CPU 33b and checks whether the measured data falls within a certain range (reference range) with respect to the target value (process 135). S-001 to S-003 in FIG. 9 almost coincide with target values and are included within a certain range. Therefore, the control device 2 continues the measurement of the coagulation time of the analysis sample (process 137). Accordingly, even in a case where the degree (X) of the interference substance is high to a certain extent, the main measurement can be performed without changing the configuration and measuring conditions of the light measuring unit 22.

On the other hand, in a case where the captured data after correction does not fall within a certain range (reference range) with respect to the target value as in S-004 of FIG. 9, the degree of the interference substance of the blood specimen to be measured is high, A sufficient measurement range cannot be secured in the main measurement. Therefore, the control device 2 stops the analysis (main measurement) before outputting an abnormal measurement result (processing 136). Thereafter, the control device 2 displays the fact that the measured coagulation time (T) or analysis (main measurement) is stopped (process 138) on the user interface screen of the display device provided in the control device 2.

Thereafter, the control device 2 determines the presence or absence of a blood specimen to be measured next (process 139) and in a case where there is a blood specimen to be measured next, dispenses the next blood specimen into the reaction container 14 (process 131). On the other hand, in a case where there is no blood specimen to be measured next, the control device 2 ends the series of measurement processes. As described above, even in a case where the degree (X) of the interference substances contained in the blood specimen is high, the measurement efficiency can be improved.

(3) Example 3

In this example, a description will be given of a blood coagulation analysis device 1 on which a signal processing portion 31 is mounted which requires fewer components as compared with the blood coagulation analysis device 1 according to Example 1 and Example 2. FIG. 10 illustrates the internal configuration of the blood coagulation analysis device 1 according to this example. In FIG. 10, components corresponding to those in FIG. 1 are denoted by the same reference numerals.

FIG. 10 illustrates a case where the measurement mechanism 21 includes four light measuring optical systems (light measuring unit 22, light source 23, and light receiving portion 24 are four, respectively). This configuration itself is the same as that of the first embodiment illustrated in FIG. 1. In a case of this example, the measurement signals from the four light receiving portions 24 are output to the amplification circuit unit 32 via a multiplexer 34. As illustrated in FIG. 10, the multiplexer 34 is provided with four switches in which only one is ON-controlled in one time division. Therefore, from the multiplexer 34, the multiplexed measurement signal S10 obtained by time division multiplexing the measurement signal S1 input from the four light receiving portions 24 is output.

The processing contents of the amplification circuit unit 32 are common to the measurement signals S1 from all the light receiving portions 24. Therefore, in this example, the amplification circuit unit 32 and the arithmetic operation unit 33 are integrated into one. Accordingly, the number of components of the signal processing portion 31 can be reduced. In other words, the number of these components can be reduced to one fourth of those of Example 1 and Example 2. In a case of this example, the CPU 33b calculates a correction data S6 in a time division manner and feeds the correction data S6 back to the amplification circuit unit 32 as the correction signal S1.

(4) Example 4

In the examples described above, although a case where the degree (X) of the interference substance is obtained by calculation prior to the start of the main measurement has been described, in this example, a blood coagulation analysis device 1 for estimating the interference substances contained in the blood specimen based on the detected degree (X) of the interference substance will be described.

FIG. 11 illustrates the configuration of the blood coagulation analysis device 1 according to this example. In FIG. 11, portions corresponding to those in FIG. 1 are denoted by the same reference numerals. In this example, the measurement mechanism 21 includes three scattered light measuring optical systems and one transmitted light measuring optical system. In the transmitted light measuring optical system, as illustrated in FIG. 11, the light source 23 and the light receiving portion 24a are disposed at positions facing each other across the light measuring unit 22a.

In a reason why the degree (X) of the interference substance is high and it is determined that this measurement is affected, there is a case due to the effects of such precipitation or bubbles of fibrin. in addition to the fats and oils (for example, chyle). In a case of estimating this cause, the control device 2 relocates the reaction container 14 into which the blood specimen is dispensed to the light measuring unit 22a by the reaction container transfer mechanism 11. Thereafter, the control device 2 dispenses a reagent corresponding to the diluent liquid and the interference substance to be measured (for example, triglyceride, etc.) to the blood specimen using the coagulation analysis reagent dispensing mechanism 16 with respect to the blood specimen and the absorbance thereof is measured by the light receiving portion 24a. The control device 2 estimates the interference substance to be measured based on the measured absorbance information.

(5) Example 5

In Example 4 described above, although the transmitted light measuring optical system (light measuring unit 22a, light source 23, light receiving portion 24a) dedicated to the estimation of the interference substances is disposed in the blood coagulation analysis device 1, it is not always necessary to dispose the transmitted light measuring optical system dedicated to the estimation of the interference substance. For example, even in a composite type automatic analysis device that can measure both blood coagulation items and biochemical analysis items, a mechanism for measuring biochemical analysis items can be used for estimating interference substances contained in the blood specimen.

FIG. 12 illustrates a schematic configuration of the composite type automatic analysis device 1100. The composite type automatic analysis device 1100 mainly includes a specimen dispensing probe 1101 (corresponding to the specimen dispensing portion 15), a specimen disc 1102 (corresponding to specimen erection portion 17), a reagent dispensing probe 1106 (corresponding to coagulation analysis reagent dispensing mechanism 16), the reagent disc 1107, the reaction container stock portion 1111 (corresponding to reaction container erection portion 13), the reaction container transport mechanism 1112 (corresponding to reaction container transfer mechanism 11 and reaction container holding mechanism 12), the signal processing portion 1121 (corresponding to signal processing portion 31), a reaction container disposal portion 1117, an operation portion 1118, a storage portion 1119, and a control unit 1120.

The specimen dispensing probe 1101 adsorbs a specimen (sample) accommodated in a specimen container (sample container) 1103 disposed on a specimen disc 1102 rotating in a clockwise direction and a counterclockwise direction and an accuracy management sample accommodated in an accuracy management sample container (not illustrated) and discharges the specimen or the accuracy management sample to the reaction container 1104 (corresponding to the reaction container 14). The specimen dispensing probe 1101 is connected to the specimen syringe pump 1105 and adsorbs or discharges the specimen under the control of a computer which is the control unit 1120.

The reagent dispensing probe 1106 adsorbs the reagent accommodated in the reagent container 1108 disposed on the reagent disc 1107 and discharges the reagent to the reaction container 1104 in which the specimen is accommodated. Here, the mixed solution between the specimen (also including diluted liquid of specimen) and the reagent to each other is referred to as "reaction solution". The reagent dispensing probe 1106 is connected to the reagent syringe pump 1110, and adsorbs or discharges the reagent under the control of a computer which is the control unit 1120.

For the blood coagulation analysis, a reagent temperature raising mechanism 1109 can be built in the reagent dispensing probe 1106. By the control unit 1120 controlling the reagent temperature raising mechanism 1109, the temperature of the reagent absorbed by the reagent dispensing probe 1106 is raised and adjusted to an appropriate temperature (predetermined temperature).

The reaction container transport mechanism 1112 transports and installs the reaction container 1104. The reaction container transport mechanism 1112 holds the reaction container 1104, rotates horizontally to transport and install the reaction container 1104 from the reaction container stock portion 1111 to a reaction container installation portion 1114 of the detection unit 1113. In addition, the reaction container transport mechanism 1112 transports and installs the reaction container 1104 to a reaction container installation portion 1129 of a biochemical reaction disc 1126. The reaction container installation portion 1114 here corresponds to the light measuring unit 22 in Example 4. In addition, the reaction container installation portion 1129 corresponds to the light measuring unit 22a of Example 4.

The detection unit 1113 has at least one reaction container installation portion 1114 (a case of one reaction container installation portion is in FIG. 12) for placing the reaction container 1104 and measures the scattered light from the reaction container 1104 inserted into the reaction container installation portion 1114. The light source 1115 (corresponding to the light source 23 in FIG. 1) of the detection unit 1113 irradiates the reaction container 1104 with the irradiation light. The irradiation light irradiated from the light source 1115 is scattered by the reaction solution contained in the reaction container 1104. The detection unit 1116 (light receiving portion 24 in FIG. 11) includes a photodiode or the like. The detection unit 1116 receives the scattered light scattered by the reaction solution in the reaction container 1104 and performs light/current conversion. Accordingly, the detection unit 1116 outputs a measurement signal indicating the received light intensity to the signal processing portion 1121 (corresponding to signal processing portion 31 in FIG. 11).

The biochemical reaction disc 1126 is kept at a constant temperature by a thermostatic bath (not illustrated). A transmitted light source 1128 is disposed inside the biochemical reaction disc 1126, and the transmitted light source 1128 irradiates the reaction container erected in the reaction container installation portion 1129 with the irradiation light. The irradiation light irradiated from the light source 1115 is attenuated by the reaction solution accommodated in the reaction container and transmitted and received by the transmitted light receiving portion 1127 (corresponding to light receiving portion 24a in FIG. 11) disposed at the facing position. The transmitted light receiving portion 1127 includes a photodiode or the like. The transmitted light receiving portion 1127 receives the transmitted light attenuated and transmitted by the reaction solution in the reaction container and converts the transmitted light into light/current. Accordingly, the transmitted light receiving portion 1127 outputs a measurement signal indicating the received light intensity to the signal processing portion 1121.

In the signal processing portion 1121, the same process as in Example 1 is executed. The processing result of the signal processing portion 1121 is output to the control unit 1120 (corresponding to control device 2 of FIG. 1) via the interface 1122. The reaction container transport mechanism 1112 holds the reaction container 1104 whose measurement is ended, transports the reaction container to the reaction container disposal portion 1117, and discards the reaction container.

The analysis items of the sample analyzed by the composite type automatic analysis device 1100 are input to the control unit 1120 via the operation screen displayed on the keyboard 1118b or the display portion 1118c as input means. A graphical user interface (GUI) for inputting analysis items by operating the analysis items displayed on the display portion 1118c with pointers or the like may be used. The control unit 1120 mainly includes an overall control unit 1120a, a measurement control unit 1120b, and the like. The overall control unit 1120a controls the operation of the composite type automatic analysis device 1100 such as dispensing of the specimen or reagent, relocation of the reaction container 1104, disposal of the reaction container 1104, and the like, which are described above.

The measurement control unit 1120b performs a calculating process of a measurement value of the light intensity changing with time according to the degree of mixing reaction between the specimen and the reagent and calculates the concentration or reaction time of an object to be analyzed (which refers to coagulation time or the like in blood coagulation measurement). Also, it is possible to calculate the concentration and the reaction time of the object to be analyzed accommodated in the specimen and to determine acceptability based on the result of comparison with a predetermined determination threshold value. The calculated concentration or reaction time is output to the display portion 1118c and stored in the storage portion 1119. The concentration or the reaction time as the calculation result may be printed out to the printer 1123 via the interface 1122.

Next, the operation of the composite type automatic analysis device 1100 will be described. In this example, measurement of the degree (X) of the interference substance based on the measurement signal of the scattered light is executed using the detection unit 1113. Similar to Example 4, in a case where it is necessary to accurately estimate the interference substance accommodated in the specimen, the sample solution adsorbed from the reaction container 1104 installed in the reaction container installation portion 1114 is dispensed into reaction containers installed on the reaction container installation portion 1129 on the biochemical reaction disc 1126. This operation corresponds to the operation of relocating the reaction container 14 to the light measuring unit 22a in Example 4.

When the reaction container in which the sample solution is dispensed moves to the reagent addition position by rotating the biochemical reaction disc 1126, the reagent dispensing probe 1106 descends to the reagent container 1108 and sorts the reagent. When the tip of the reagent dispensing probe 1106 comes into contact with the liquid surface of the reagent, since a detection signal is output from a liquid surface detection circuit (not illustrated), the control unit 1120 stops the descent operation of the reagent dispensing probe 1106 based on the output thereof.

Thereafter, the sorted reagent is dispensed into the reaction container installed in the reaction container installation portion 1129 by the reagent dispensing probe 1106, and mixed with the sample solution and the reagent. Thereafter, the mixture of the sample solution and the reagent is stirred. Subsequently, due to the rotation of the biochemical reaction disc 1126, the reaction container moves to the position of the measurement optical system (transmitted light source 1128, transmitted light receiving portion 1127) of biochemical analysis, and the absorbance thereof is measured by the transmitted light receiving portion 1127 which receives transmitted light. The measurement signal of the transmitted light is input to the control unit 1120 via the signal processing portion 1121 and the interface 1122, and the interference substance included in the specimen is estimated by the control unit 1120. The analysis result is printed out on the printer 1123, outputted on the screen of the display portion 1118*c*, or stored in the storage portion 1119.

(6) Another Example

The present invention is not limited to the examples described above, but includes various modifications. For example, the examples described above is described in detail in order to explain the present invention in an easy-to-understand manner, and it is not always necessary to provide all the configurations described. In addition, a portion of the configuration of one example can be replaced by the configuration of another example. In addition, the configuration of another example can be added to the configuration of one example. In addition, a portion of the configuration of each example can be deleted.

In addition, each configuration, functions, processing portions, processing means and the like, which are described above may be realized by hardware, for example, by designing a portion or all thereof with an integrated circuit or the like. In addition, each configuration, functions, and the like, which are described above may be realized by interpreting and executing a program that realizes the respective functions by the processor (that is, by software). Information such as programs, tables, files, and the like that realize each function can be stored in a storage device such as a memory, a hard disk, and a solid state drive (SSD), or a storage medium such as an IC card, an SD card, and a DVD. In addition, a control line and an information line indicate what is considered to be necessary for the description, all control lines and information lines necessary for the product do not indicate. In fact, it can be considered that almost all the configurations are connected to each other.

REFERENCE SIGNS LIST

1 . . . blood coagulation analysis device
2 . . . control device
11 . . . reaction container transfer mechanism
12 . . . reaction container holding mechanism
13 . . . reaction container erection portion
14 . . . reaction container
15 . . . specimen dispensing portion
16 . . . coagulation analysis reagent dispensing mechanism
17 . . . specimen erection portion
18 . . . specimen container
19 . . . specimen dispensing mechanism
21 . . . measurement mechanism
22 . . . light measuring unit
22*a* . . . light measuring unit
23 . . . light source
24 . . . light receiving portion
24*a* . . . light receiving portion
25 . . . irradiation light
26 . . . scattered light
31 . . . Signal processing portion
32 . . . amplification circuit unit
32*a* . . . preamplifier
32*b* . . . adder/subtracter
32*c* . . . amplification circuit
33 . . . arithmetic operation unit
33*a* . . . analog/digital conversion circuit
33*b* . . . CPU
33*c* . . . memory
33*d* . . . digital/analog conversion circuit
33*e* . . . adjustment circuit
34 . . . multiplexer
1100 . . . composite type automatic analysis device
1101 . . . specimen dispensing probe (specimen dispensing mechanism)
1102 . . . specimen disc
1103 . . . specimen container (sample container)
1104 . . . reaction container (coagulation)
1105 . . . specimen syringe pump
1106 . . . reagent dispensing probe (reagent dispensing mechanism)
1107 . . . reagent disc
1108 . . . reagent container
1109 . . . reagent temperature raising mechanism
1110 . . . reagent syringe pump
1111 . . . reaction container stock portion
1112 . . . reaction container transport mechanism
1113 . . . detection unit
1114 . . . reaction container installation portion
1115 . . . light source
1116 . . . detection unit (optical sensor)
1117 . . . reaction container disposal portion
1118 . . . operation portion
1118*a* . . . mouse
1118*b* . . . keyboard
1118*c* . . . display portion
1119 . . . storage portion
1120 . . . control unit
1120*a* . . . overall control unit
1120*b* . . . measurement control unit
1121 . . . signal processing portion
1122 . . . interface
1123 . . . printer
1126 . . . biochemical reaction disc
1127 . . . transmitted light receiving portion
1128 . . . transmitted light source
1129 . . . reaction container installation portion

The invention claimed is:

1. An automatic analysis device comprising:
a measurement mechanism that has a light source which irradiates a reaction container containing a specimen with light, and a photodetector which detects scattered light from the specimen in the reaction container;
an amplification circuit configured to receive a first measurement signal from the photodetector, amplify the first measurement signal with a fixed amplification rate, and output the amplified first measurement signal as a second measurement signal;
a processor programmed to confirm a stability of the second measurement signal, and, after confirming the stability of the second measurement signal, calculate a correction signal based on a difference between a signal level of the second measurement signal and a predetermined target value and output the correction signal to the amplification circuit; and
an adder/subtracter configured to receive the first measurement signal from the photodetector, add or subtract the correction signal to or from the first measurement signal, and output a corrected first measurement signal;
a controller that controls operations of the measurement mechanism, the adder/subtracter, the amplification circuit, and the processor, wherein the amplification circuit is configured to amplify the corrected first measurement signal from the adder/subtracter with the fixed amplification rate and output the amplified corrected first measurement signal as a corrected second measurement signal, wherein the processor is further programmed to confirm a stability of the corrected second measurement signal and, after confirming the stability of the corrected second measurement signal, execute an analysis operation on the specimen based on the corrected second measurement signal, wherein confirming a stability of a signal includes determining, based on whether or not a deviation of two or more consecutive or intermittent data of the signal is within a preset range, the signal being stable if the deviation is within the preset range, and wherein executing the analysis operation on the specimen comprises determining a degree of an interference substance contained in the specimen based on the corrected second measurement value.

2. The automatic analysis device according to claim 1, wherein the processor is programmed to, after confirming the stability of the corrected second measurement signal, determine the degree of interference substance contained in the specimen, based on the corrected second measurement value obtained from the first corrected measurement value output from the adder/subtracter, without switching the wavelength of the light source at a time of coagulation time measurement to obtain the first measurement signal and without providing a second photodetector for measuring the degree of the interference substance separately from the photodetector which detects the scattered light from the specimen in the reaction container.

3. The automatic analysis device according to claim 1, wherein the processor is further programmed to:
execute the analysis operation when the degree of the interference substance is less than or equal to a first threshold value, and
stop the analysis operation when the degree of the interference substance is larger than a first threshold value.

4. The automatic analysis device according to claim 1, wherein the processor is further programmed to:
execute the analysis operation when the degree of the interference substance is less than or equal to a first threshold value and less than or equal to a second threshold value,
output an alarm indicating that the degree of the interference substance contained in the specimen is high when the degree of the interference substance is less than or equal to the first threshold and larger than the second threshold value, and
stop the analysis operation when the degree of the interference substance is larger than the first threshold value.

5. The automatic analysis device according to claim 1, wherein the reaction container contains the specimen mixed with a reagent.

6. The automatic analysis device according to claim 5, wherein the processor is further programmed to:
after confirming the stability of the corrected second measurement signal, determine a degree of an interference substance contained in the specimen based on the corrected second measurement value,
execute the analysis operation based on the degree of the interference substance when the degree of the interference substance is less than or equal to a first threshold value, and
stop the analysis operation when the degree of the interference substance is larger than the first threshold value.

7. The automatic analysis device according to claim 5, wherein the processor is further programmed to:
after confirming the stability of the corrected second measurement signal, determine a degree of an interference substance contained in the specimen based on the corrected second measurement value,
execute the analysis operation based on the degree of the interference substance when the degree of the interference substance is less than or equal to a first threshold value and less than or equal to a second threshold,
output an alarm when the degree of the interference substance is less than or equal to the first threshold and larger than the second threshold value, and
stop the analysis operation when the degree of the interference substance is larger than the first threshold value.

8. The automatic analysis device according to claim 1, further comprising:
a multiplexer that multiplexes by time division and outputs a plurality of the first measurement signals outputted from a plurality of the photodetectors corresponding to a plurality of the light measuring units,
wherein the adder/subtracter, the amplification circuit, and the processor commonly process the plurality of first measurement signals sequentially input from the multiplexer in a time division manner.

9. The automatic analysis device according to claim 1, wherein the measurement mechanism further includes another photodetector which detects transmitted light transmitted through the reaction container.

10. The automatic analysis device according to claim 9, wherein the processor is further programmed to:
after confirming the stability of the corrected second measurement signal, determine a degree of an interference substance contained in the specimen based on the corrected second measurement value, and
when the degree of the interference substance is larger than a first threshold value, measure the transmitted light detected by the other photodetector.

11. The automatic analysis device according to claim 9, wherein the other photodetector is provided in a biochemical analysis disc.

12. The automatic analysis device according to claim 1, wherein the executing the analysis operation on the specimen comprises controlling an operation of a reaction container transfer mechanism, an operation of a reaction container holding mechanism, an operation of a specimen dispensing portion, an operation of a coagulation analysis reagent dispensing mechanism, an operation of a specimen erection portion, an operation of a specimen dispensing mechanism, an operation of a measurement mechanism, an operation of a signal processing portion, an operation of a pump, an operation of a washing mechanism, and an washing water supply operation.

13. An automatic analysis system comprising:
an automatic analysis device; and
a control device that controls an operation of the automatic analysis device,
wherein the automatic analysis device includes:
a measurement mechanism that has a light source which irradiates a reaction container containing a specimen with light, and a photodetector which detects scattered light from the specimen in the reaction container,
an amplification circuit configured to receive a first measurement signal from the photodetector, amplify the first measurement signal with a fixed amplification rate, and output the amplified first measurement signal as a second measurement signal,
a processor programmed to confirm a stability of the second measurement signal, and, after confirming the stability of the second measurement signal, calculate a correction signal based on a difference between a signal level of the second measurement signal and a predetermined target value and output the correction signal to the amplification circuit, and
an adder/subtracter configured to receive the first measurement signal from the photodetector, add or subtract the correction signal to or from the first measurement signal, and output a corrected first measurement signal;
wherein the amplification circuit is configured to amplify the corrected first measurement signal from the adder/subtracter with the fixed amplification rate and output the amplified corrected first measurement signal as a corrected second measurement signal,
wherein the processor is further programmed to confirm a stability of the corrected second measurement signal and, after confirming the stability of the corrected second measurement signal, execute an analysis operation on the specimen based on the corrected second measurement signal, and
wherein confirming a stability of a signal includes determining, based on whether or not a deviation of two or more consecutive or intermittent data of the signal is within a preset range, the signal being stable if the deviation is within the preset range, and
wherein executing the analysis operation on the specimen comprises determining a degree of an interference substance contained in the specimen based on the corrected second measurement value.

14. The automatic analysis device according to claim 13, wherein the processor is programmed to, after confirming the stability of the corrected second measurement signal, determine the degree of interference substance contained in the specimen based on the corrected second measurement value obtained from the first corrected measurement value output from the adding or subtracting, without switching the wavelength of the light source at a time of coagulation time measurement to obtain the first measurement signal and without providing a second photodetector for measuring the degree of the interference substance separately from the photodetector which detects the scattered light from the specimen in the reaction container.

15. The automatic analysis device according to claim 13, wherein the processor is further programmed to:
execute the analysis operation when the degree of the interference substance is less than or equal to a first threshold value, and
stop the analysis operation when the degree of the interference substance is larger than a first threshold value.

16. The automatic analysis device according to claim 13, wherein the processor is further programmed to:
execute the analysis operation when the degree of the interference substance is less than or equal to a first threshold value and less than or equal to a second threshold value,
output an alarm indicating that the degree of the interference substance contained in the specimen is high when the degree of the interference substance is less than or equal to the first threshold and larger than the second threshold value, and
stop the analysis operation when the degree of the interference substance is larger than the first threshold value.

* * * * *